United States Patent
Jayasundera et al.

(10) Patent No.: US 10,457,113 B2
(45) Date of Patent: Oct. 29, 2019

(54) VEHICLE EXTREME TEMPERATURE SAFETY SYSTEMS AND METHODS

(71) Applicant: Braeburn Inc., Johns Creek, GA (US)

(72) Inventors: Gihan Jayasundera, Johns Creek, GA (US); Nayana Jayasundera, Johns Creek, GA (US)

(*) Notice: Subject to any disclaimer, the term of this patent is extended or adjusted under 35 U.S.C. 154(b) by 416 days.

(21) Appl. No.: 15/056,217

(22) Filed: Feb. 29, 2016

(65) Prior Publication Data
US 2017/0028811 A1 Feb. 2, 2017

Related U.S. Application Data

(60) Provisional application No. 62/121,657, filed on Feb. 27, 2015.

(51) Int. Cl.
*B60H 1/00* (2006.01)
*A61B 5/00* (2006.01)
*A61B 5/01* (2006.01)

(52) U.S. Cl.
CPC ....... *B60H 1/00742* (2013.01); *A61B 5/0075* (2013.01); *A61B 5/01* (2013.01); *A61B 5/6893* (2013.01); *B60H 1/00778* (2013.01); *B60H 1/00821* (2013.01); *B60H 1/00878* (2013.01); *A61B 2503/12* (2013.01); *A61B 2560/0252* (2013.01); *A61B 2562/0204* (2013.01); *A61B 2562/0247* (2013.01)

(58) Field of Classification Search
CPC ............ B60H 1/00742; B60H 1/00778; B60H 1/00821; A61B 5/0075; A61B 5/01; A61B 5/6893

USPC .......................................... 165/202, 203, 204
See application file for complete search history.

(56) References Cited

U.S. PATENT DOCUMENTS

| | | | | |
|---|---|---|---|---|
| 4,920,759 A | * | 5/1990 | Tanaka | B60H 1/00478 165/203 |
| 6,202,934 B1 | * | 3/2001 | Kamiya | B60H 1/00735 165/204 |
| 6,480,103 B1 | * | 11/2002 | McCarthy | E05B 83/26 340/425.5 |
| 6,485,081 B1 | * | 11/2002 | Bingle | E05B 83/26 292/DIG. 43 |
| 6,639,512 B1 | | 10/2003 | Lee et al. | |
| 6,659,358 B2 | * | 12/2003 | Kamiya | B60H 1/00792 165/204 |

(Continued)

OTHER PUBLICATIONS

International Search Report dated May 17, 2016, for corresponding International Application No. PCT/US2016/020061.

*Primary Examiner* — Ljiljana V. Ciric
(74) *Attorney, Agent, or Firm* — Gary Baker; QIPLG

(57) ABSTRACT

Safety systems and methods to prevent or mitigate thermal stress conditions in a vehicle. The systems include sensors to detect conditions in and around a vehicle, particularly the temperature inside the vehicle and the condition of occupants. System controllers receive the sensor information, determine the thermal stress status of occupants, and activate appropriate actuators configured to reduce thermal stress in the vehicle. The methods include providing the system, detecting a vehicle occupant surface temperature, using the detected temperature to determine a body core temperature, and activating an actuator if the occupant body core temperature is determined to be out of a preset range.

17 Claims, 2 Drawing Sheets

(56) References Cited

U.S. PATENT DOCUMENTS

| | | | |
|---|---|---|---|
| 6,719,624 B2 * | 4/2004 | Hayashi | B60H 1/00285 454/120 |
| 6,971,446 B2 * | 12/2005 | Price | B60H 1/00742 165/202 |
| 7,246,656 B2 * | 7/2007 | Ichishi | B60H 1/00792 165/202 |
| 9,632,666 B2 * | 4/2017 | Goldman-Shenhar | G06F 3/0484 |
| 9,862,245 B2 * | 1/2018 | Kim | B60H 1/00742 |
| 9,862,247 B2 * | 1/2018 | Perkins | B60H 1/00871 |
| 10,179,499 B2 * | 1/2019 | Perkins | B60H 1/00871 |
| 10,194,871 B2 * | 2/2019 | Newberry | A61B 5/6893 |
| 10,227,063 B2 * | 3/2019 | Abreu | B60H 1/00742 |
| 10,238,346 B2 * | 3/2019 | Newberry | G16H 40/63 |
| 10,272,739 B2 * | 4/2019 | Boehme | B60H 1/00742 |
| 10,275,959 B2 * | 4/2019 | Ricci | H04W 4/21 |
| 2001/0022222 A1 * | 9/2001 | Aoki | B60H 1/00285 165/203 |
| 2002/0161501 A1 | 10/2002 | Dulin et al. | |
| 2003/0102688 A1 * | 6/2003 | Bingle | E05B 83/26 296/76 |
| 2003/0109212 A1 * | 6/2003 | Hayashi | B60H 1/00285 454/56 |
| 2003/0172156 A1 * | 9/2003 | Price | B60H 1/00742 709/225 |
| 2004/0074244 A1 * | 4/2004 | Ichishi | B60H 1/00742 62/186 |
| 2004/0079099 A1 * | 4/2004 | Kumada | B60H 1/00742 62/244 |
| 2005/0103488 A1 * | 5/2005 | Ichishi | B60H 1/00792 165/202 |
| 2005/0194125 A1 * | 9/2005 | Asai | B60H 1/00792 165/202 |
| 2005/0267646 A1 * | 12/2005 | Ichishi | B60H 1/00742 700/300 |
| 2006/0290518 A1 | 12/2006 | Bingle et al. | |
| 2007/0114292 A1 * | 5/2007 | Breed | B60H 1/00742 236/49.3 |
| 2007/0273504 A1 * | 11/2007 | Tran | A61B 5/0022 340/539.12 |
| 2008/0069403 A1 * | 3/2008 | Breed | B60K 28/066 382/104 |
| 2008/0143085 A1 * | 6/2008 | Breed | B60R 21/01516 280/735 |
| 2008/0195261 A1 * | 8/2008 | Breed | B60R 21/0132 701/2 |
| 2008/0234899 A1 * | 9/2008 | Breed | B60N 2/002 701/47 |
| 2008/0236275 A1 * | 10/2008 | Breed | B60C 11/24 73/290 V |
| 2009/0066065 A1 * | 3/2009 | Breed | B60J 10/00 280/735 |
| 2009/0092284 A1 * | 4/2009 | Breed | B60J 10/00 382/103 |
| 2009/0156988 A1 * | 6/2009 | Ferren | A61B 5/0031 604/65 |
| 2009/0284378 A1 * | 11/2009 | Ferren | G08B 21/06 340/573.1 |
| 2009/0287093 A1 * | 11/2009 | Ferren | A61B 5/412 600/481 |
| 2009/0287094 A1 * | 11/2009 | Ferren | A61B 5/026 600/481 |
| 2009/0287101 A1 * | 11/2009 | Ferren | A61B 5/0031 600/504 |
| 2009/0287109 A1 * | 11/2009 | Ferren | A61B 5/0031 600/549 |
| 2009/0287110 A1 * | 11/2009 | Ferren | A61B 5/6887 600/549 |
| 2009/0287191 A1 * | 11/2009 | Ferren | A61B 5/0031 604/891.1 |
| 2009/0292212 A1 * | 11/2009 | Ferren | A61B 5/0205 600/481 |
| 2009/0292213 A1 * | 11/2009 | Ferren | A61B 5/0031 600/481 |
| 2009/0292214 A1 * | 11/2009 | Ferren | A61B 5/0031 600/481 |
| 2009/0292222 A1 * | 11/2009 | Ferren | A61B 5/0031 600/549 |
| 2010/0036209 A1 * | 2/2010 | Ferren | A61B 5/0002 600/301 |
| 2010/0036263 A1 * | 2/2010 | Ferren | A61B 5/0002 600/481 |
| 2011/0066051 A1 * | 3/2011 | Moon | A61B 5/0002 600/509 |
| 2012/0242501 A1 * | 9/2012 | Tran | A61B 5/0024 340/870.02 |
| 2013/0037252 A1 * | 2/2013 | Major | B60H 1/00742 165/202 |
| 2013/0124038 A1 * | 5/2013 | Naboulsi | B60R 11/0264 701/36 |
| 2013/0255930 A1 * | 10/2013 | Prakah-Asante | B60H 1/00742 165/203 |
| 2013/0306297 A1 * | 11/2013 | Sebastian | B60H 1/00971 165/202 |
| 2013/0314536 A1 * | 11/2013 | Frank | H04N 5/33 348/148 |
| 2013/0342691 A1 * | 12/2013 | Lewis | H04N 5/332 348/143 |
| 2014/0093133 A1 * | 4/2014 | Frank | B60R 21/01532 382/104 |
| 2014/0148881 A1 | 5/2014 | Roth et al. | |
| 2014/0306799 A1 * | 10/2014 | Ricci | H04W 4/21 340/5.83 |
| 2014/0306826 A1 * | 10/2014 | Ricci | H04W 4/21 340/573.1 |
| 2014/0309806 A1 * | 10/2014 | Ricci | B60Q 1/00 701/1 |
| 2015/0075763 A1 * | 3/2015 | Kim | B60H 1/00742 165/203 |
| 2015/0094914 A1 * | 4/2015 | Abreu | B60H 1/00742 701/41 |
| 2015/0105687 A1 * | 4/2015 | Abreu | A61B 5/01 600/549 |
| 2016/0054023 A1 * | 2/2016 | Baker | E04F 19/00 307/31 |
| 2016/0082808 A1 * | 3/2016 | Perkins | B60H 1/00742 165/11.2 |
| 2017/0088098 A1 * | 3/2017 | Frank | G06K 9/00362 |
| 2017/0124842 A1 * | 5/2017 | Sinha | G05B 19/048 |
| 2018/0326814 A1 * | 11/2018 | Prakah-Asante | B60H 1/00742 |
| 2018/0330811 A1 * | 11/2018 | Macary | G06Q 10/0639 |
| 2019/0084372 A1 * | 3/2019 | Gallagher | G06K 9/2018 |

* cited by examiner

VEHICLE EXTREME TEMPERATURE SAFETY SYSTEMS AND METHODS

FIELD OF THE INVENTION

The inventions relate to systems of interacting components adapted to detect, warn, and mitigate heat and cold stress hazards to occupants of vehicles. A controller receives information from various sensors and signals actuators to take steps reducing heat buildup and to warn persons of present temperature stress dangers. Methods include, e.g., detecting the presence of an occupant in a vehicle, detecting vehicle interior temperature, detecting the body temperature of the occupant, determining existing or impending heat stress danger, and taking steps to prevent excessive heat exposure to the occupant.

BACKGROUND OF THE INVENTION

The problem of children or pets left in vehicles under heat stress conditions has rightly received significant attention. In many states it is illegal to leave occupants in a car under conditions that may result in significant heat stress. Often merely cracking a window is inadequate to protect occupants, e.g., parked in direct sunlight. Every year, dozens of lives are lost because of heat exhaustion that could have been prevented had appropriate warnings or actions been initiated in time.

Systems are available in some high end cars to turn on a vent fan at a certain time of day, e.g., so that the driver can enter a pre-cooled vehicle. However, these systems are incapable of recognizing a heat stress condition or of taking appropriate actions to mitigate heat stress to a vehicle occupant.

In Dunlin (U.S. Pat. No. 6,922,622) hot vehicle systems are described, e.g., wherein persons are detected by seat sensors, but there is no direct detection of the person's condition.

In view of the above, we see a need for systems that gather sensor inputs and determine appropriate actuator outputs, e.g., depending on the condition of the occupants. We believe benefits could also be realized through systems that make an evaluation of the heat or cold stress condition of occupants in consideration of actions to be taken. The present invention provides these and other features that will be apparent upon review of the following.

SUMMARY OF THE INVENTION

The present inventions include systems and methods to detect and prevent development of thermal stress in occupants of a vehicle. The systems can include sensors to detect parameters indicative of thermal stress conditions, actuators to take appropriate actions to prevent or remediate thermal stress conditions, and a controller to interpret sensor inputs and instruct the actuators to act in reducing thermal stress in the vehicle.

The systems for preventing excessive heat or cold exposure to occupants of a vehicle can include an occupancy sensor, an occupant body temperature sensor, a controller configured to receive signals from the occupancy sensor, and body temperature sensor, and one or more actuator to provide a response to an over heat or cold condition. The controller can be configured to determine an occupant temperature from the body temperature sensor when the controller receives an occupant present signal from the occupancy sensor. Further, the controller can be configured to activate the actuator when the determined occupant body temperature goes outside a preset temperature range.

Sensors in the system can provide signals relevant to determination of a possible thermal stress danger. For example, system sensors can include a vehicle interior temperature sensor. The system controller can be configured to only activate a particular actuator if an interior temperature detected by the interior temperature sensor falls outside a preset range. The system sensors can include a microphone or seat pressure sensor to signal the presence of a vehicle occupant. An important sensor can be one or more sensors capable of indicating an occupant body temperature, thus providing direct verification of an occupant's level of thermal stress. A preferred occupant body temperature sensor can be an infrared light sensor configured to measure a temperature of a body surface.

In an alternate embodiment, if the sensors detect cold temperatures below a set parameter, the controller can trigger the actuators to provide a warning or call for aid. For example, if the occupant goes in to hypothermia, e.g., below 95 degrees Fahrenheit and 89 degrees in extreme hypothermia, a call can go out for emergency response team in the closest vicinity based on the closest mobile cell tower and GPS location.

Controllers can be programmed to take appropriate action on the input of particular circumstances. For example, a controller can be configured to receive a body temperature signal ranging from 25° C. to 45° C.; the controller set to activate an appropriate actuator response when an occupant body temperature exceeds 39° C. or falls below 35° C. Such body core temperatures can be indicated by reference to occupant body surface temperatures, e.g., ranging outside 40° C. to 30° C., respectively.

Actuators can be capable of taking actions to protect occupants from thermal stress, e.g., that can be developed in a closed car exposed to direct sunlight. For example, actuators can include one or more controller actuated cell phones, window motors, vent fans, and/or a sirens.

The inventions include methods of using the present systems to prevent excessive heat or cold exposure to occupants in vehicles. Methods can include, e.g., preventing excessive heat or cold exposure to occupants of a vehicle by providing a system with an occupancy sensor, an occupant body temperature sensor configured to detect absolute or relative temperature, an actuator, and a controller configured to receive signals from the occupancy sensor, and body temperature sensor. When an occupant present signal is received from the occupancy sensor, an occupant body temperature can be determined from the body temperature sensor. If the occupant body temperature is determined to exceed a preset temperature range, an appropriate actuator is activated to relieve thermal stress on the occupant.

Receiving an occupant present signal can include the controller receiving a signal from, e.g., an infrared light sensor, a pressure sensor, and ultrasonic microphone, and an audio microphone.

Determining the occupant body temperature can include, e.g., detecting an infrared light spectrum emitted from a surface of the occupant, or direct or indirect (e.g., through apparel) contact of the occupant with a temperature sensor.

Activating the actuator can include, e.g., energizing an electric window motor, energizing a fan motor, energizing a heating system, dialing a phone number, energizing an audio speaker, and/or the like.

Definitions

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a surface" can include a combination of two or more surfaces; reference to "signals" includes mixtures of signals, and the like.

Unless defined otherwise, all technical and scientific terms used herein have the same meaning as commonly understood by one of ordinary skill in the art to which the invention pertains. Although any methods and materials similar or equivalent to those described herein can be practiced without undue experimentation based on the present disclosure, preferred materials and methods are described herein. In describing and claiming the present invention, the following terminology will be used in accordance with the definitions set out below.

Thermal stress to an occupant can result in body temperatures outside the normal range. Excessive heat stress can lead to heat prostration (exhaustion). Excessive cold stress can lead to hypothermia in an occupant.

Excessive heat exposure and heat stress are present in an environment when a person in the environment is expected to have difficulty maintaining normal physiology due to the temperature (e.g., and humidity) of the environment. Heat stress can raise the body temperature and/or cause electrolyte imbalances, e.g., leading to heat cramps, heat exhaustion, or heat stroke. Heat exhaustion is the body's response to an excessive loss of the water and salt, usually through excessive sweating. Heat stroke is the most serious heat-related stress occurring when the body becomes unable to control its temperature. In heat stroke, the body's temperature can rise rapidly, the sweating mechanism failing, and the body is unable to cool down. When heat stroke occurs, the body temperature can rise to 106 degrees Fahrenheit or higher within 10 to 15 minutes. Heat stroke can cause death or permanent disability unless heat stress conditions are not mitigated and emergency treatment given.

Excessive cold exposure and hypothermia risk are present in an environment when a person in the environment is expected to have difficulty retaining adequate body heat due to a low temperature of the environment. Cold environments can lower the body temperature, e.g. bringing shivering and muscle mis-coordination. Surface blood vessels contract as the body focuses warm blood on the brain and core. This makes hypothermia particularly well identifiable using the systems and methods of the invention. Further, the occupant can become pale, with exposed body surfaces becoming blue. Hypothermia can cause death in short order unless the occupant is treated by exposure to warmer conditions.

Body temperature is the temperature of a person, as measured in a clinical environment. Body temperature is intended to represent the body core temperature, classically 98.6° F. In most circumstances body surface temperature is typically somewhat lower than the body temperature, and can vary significantly depending on the body surface (skin) measured. The body temperature can be inferred from the body surface temperature. In cold climates, the body surface temperature is often lower than the body core temperature. Given the ambient temperature and body surface temperature, inferences can be made as to the body core temperature of a vehicle occupant.

The interior temperature of a vehicle is the temperature of air in the passenger compartment.

A vehicle is a means of transportation intended to move one or more persons. For example, vehicles can include automobiles, trucks, tractors, agricultural equipment, boats, and the like.

A vehicle is occupied if there is an animal (e.g., human or pet) in the vehicle. An occupancy sensor can detect the presence of an animal in the vehicle, e.g., passenger compartment.

DETAILED DESCRIPTION

The present systems and methods are directed to detection and alleviation of thermal stress conditions in vehicles, particularly in the presence of occupants. The systems can detect temperature, and changes in temperature, of the vehicle interior and or of the vehicle occupants. The systems include a controller configured to evaluate inputs to determine if a thermal stress danger exists for any occupant present. The controller can be configured to take action to protect the occupant from harm due to the thermal stress. Methods of preventing thermal stress for occupants of a vehicle can include, e.g., using sensor hardware to evaluate conditions in a vehicle and the thermal stress status of occupants, identifying combinations of conditions that suggest a thermal stress hazard, and energizing hardware that mitigates the thermal stress condition, e.g., by heating or cooling the interior of the vehicle, and informing persons of the vehicle or occupant conditions.

I. Systems.

Figure 1:
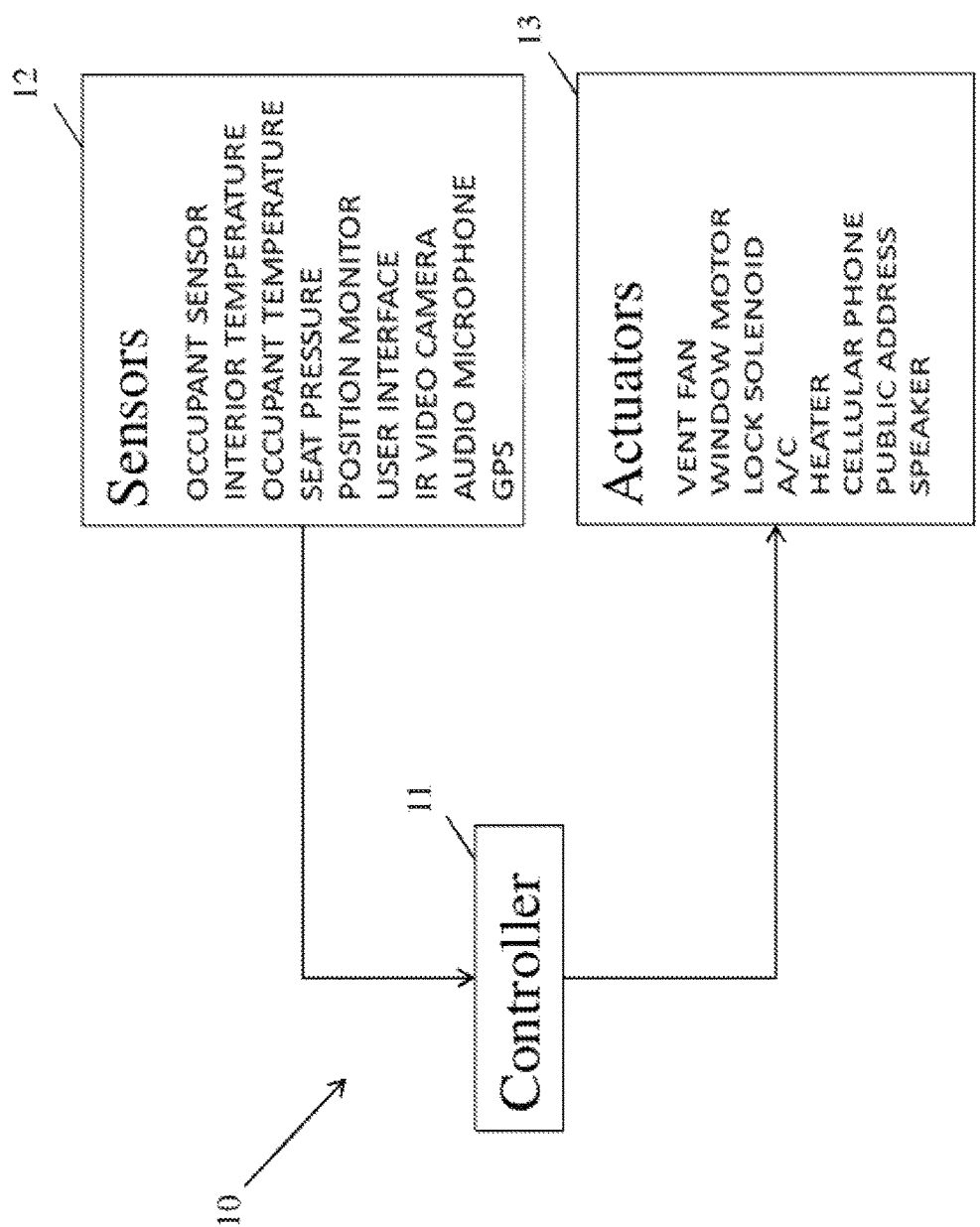
FIG. 1 is a diagram of exemplary car thermal safety system hardware, including applicable subsystems.

In general, the thermal stress avoidance and remedial systems can monitor the interior of a vehicle to determine the presence of an occupant, the status of vehicle systems, the interior temperature of the vehicle, and the body temperature of the occupant. The system can determine whether a combination of detected conditions represents a thermal stress danger to the occupant. Once a thermal stress threat has been identified, the system controller can take appropriate actions to mitigate the stress or provide aid to the occupant. As shown in FIG. 1, the systems 10 to detect and mitigate thermal stress on vehicle occupants generally includes a controller 11 receiving signals from sensors 12, and instructing appropriate activities from actuators 13.

Sensors.

The controller can rely on multiple sensors to initiate appropriate actions according to the conditions in a vehicle. Sensors can be provided to determine the condition of the vehicle environment, the number of occupants, and the condition of the occupants. For example, the system can include mechanical sensors to detect a body weight in a seat, thermometers, relative humidity detectors, audio sensors, video sensors, and a user interface. Temperatures can be detected, e.g., using thermometers or infrared light detectors. The condition of the vehicle can be determined, e.g., by command history, microswitches, or position monitors that indicate the condition of vehicle utilities, such as windows and fans.

The status of the vehicle can be determined by sensors. For example, it can be important to heat stress remediation whether or not the car is moving, whether the AC system is running, what fans are on, and what windows are open. Much of this may be a matter of record and available from the vehicle's central computer. Optionally, a separate array of sensors can be dedicated to the present systems to obtain this information, as necessary.

The systems can detect the presence of an occupant by using a mechanical pressure sensor located in or on one or more of the vehicle seats. For example, a sensor in or under the seat cushion can detect the presence of a person sitting on the seat. A spring loaded sensor can provide a threshold compression signal, or a varying signal, e.g., depending on the weight of the person seated in the seat. The sensor can be, e.g., hydraulic, pneumatic, or piezoelectric. The sensor can optionally detect the presence of a person by a change in capacitance or resistance of an electronic element in the seat. Sensors detecting the size of the occupant can be used to appropriately direct the field of view for certain optical or video sensors.

The presence of a person or animal can be detected from analysis of an audio signal. An audio microphone can be monitored for frequencies or tone variations characteristic of speech or other occupant audio. Optionally, ultrasonic or radar motion sensors can be used to detect the presence of occupants.

Video signals can be monitored to detect the presence of a vehicle occupant. For example, video camera signals can be analyzed for the presence of shapes (e.g., facial recognition) and motions characteristic of persons or animals. Occupants may be detected by a characteristic infrared signature combination of temperature, area, sound, motion, and/or shape.

The presence of an occupant can be determined based on equipment usage or user interface inputs. For example, the presence of an occupant can be inferred from changes in the position of driver controls, seat belts, environment control systems, entertainment systems, and the like. The heat stress system itself may have an operator input (e.g., keyboard or touch sensitive screen) interface for direct confirmation of the number and type of occupants. The presence of occupants can be detected by personal RFID tags or Bluetooth devices.

The condition of the vehicle can be important to determining possible thermal stress conditions. The system can include sensors that directly or indirectly report the condition and configuration of features that can influence thermal stress dangers in the vehicle. For example, the system can monitor the position of windows, settings of fans, door latches, door locks, clocks, etc.

Temperature sensors are central to the functioning of the safety systems. The controller can receive temperature information from one or more locations to evaluate the need for a response. The temperature sensors can be, e.g., liquid filled bulb thermometers, thermisters, infrared light sensors, bimetalic strips, and or the like. The thermometers can provide the temperature of air or surfaces on the interior of the vehicle. When the vehicle interior air or surfaces fall outside a safe range, and when it has been determined one or more occupants are in the car, other system functions can be activated to confirm the presence of thermal stress and/or take actions to prevent or remedy thermal stress. In most embodiments, there is at least one temperature sensor that detects the body temperature of one or more car occupants.

Occupant body temperature detection can be by contact with the sensor, or the body temperature can be determined by detecting the amount or frequency of infrared (IR) light coming from the occupant's body. The infrared light can be near infrared IR-A: 700 nm-1400 nm (0.7 µm-1.4 µm, 215 THz-430 THz); mid infrared IR-B: 1400 nm-3000 nm (1.4 µm-3 µm, 100 THz-215 THz), or far infrared IR-C: 3000 nm-1 mm (3 µm-1000 µm, 300 GHz-100 THz). The infrared radiation can be detected by a broad view sensor, or preferably a narrow view sensor, e.g., aimed at seats known to have occupants. More sophisticated determinations of body surface temperatures can be obtained, e.g., using video sensors, such as charge coupled devices. Such video images can be analyzed for abundant information relevant to determining a heat stress condition. For example, a visible light and/or IR video can be subjected to body or face recognition algorithms, e.g., to identify the locations of occupants, size of the occupants, and locations of exposed skin on an occupant. In many cases, the body temperature is obtained by taking readings from occupant surfaces determined to be skin surfaces, preferably face surfaces.

To aid in the identification of occupants and determination of their temperature using optical (e.g., video) hardware, the vehicle environment can be readily identifiable by the hardware. For example, previously stored images of the vehicle interior can be provided to confirm new features that may be occupants. The vehicle interior may be adapted to have materials or colors discounted (e.g., green screen type technology) as occupants by the occupant detection and body temperature detection sub-systems.

Actuators.

Actuators are energized by the controller to take actions preventing or remediating thermal stress conditions inside the vehicle. Actuators can warn of a heat stress condition and/or reconfigure the vehicle to reduce the interior temperature. In a cold condition, actuators can warn of a cold stress condition and/or reconfigure the vehicle to increase the interior temperature The vehicle can be configured by actuators to cool or warm the interior. Such actuators can be associated with the air conditioning system, heating system, vent system, windows, moon roof, window tinting, seat heating system, window shading, door locks, door latches, automatic door features, and/or the like. When an occupant body temperature (e.g., as detected at the skin) surpasses a high or low threshold, and/or a combination of sensory parameters signal a thermal stress condition, the controller can command actuators to, e.g., turn on heaters, turn on fans directing outside air into the vehicle interior, and open or close one or more windows, as appropriate. Actuators can unlock doors so occupants can leave the vehicle.

Another group of actuators includes communication devices to warn occupants, or outside persons, of a thermal stress condition. For example, an audio warning device (e.g., siren or speech system) can be activated to tell the occupant or a current or impending thermal stress condition. The controller can activate an emergency communication device, such as a phone or other radio system, to notify police, emergency specialists, or owners of the vehicle of detected adverse conditions in the vehicle.

Controllers.

Digital or analog logic devices can act as controllers in the systems of the inventions. The controllers can receive signals from the system sensors, review the conditions to determine a level of thermal stress to which a vehicle occupant may be exposed, and take action to relieve the occupant of thermal stress dangers.

Controllers of the inventions are typically computers or interfaced CPUs. For example, the controllers can be electric logic devices with software programming and hardware capable of receiving data (e.g., from sensor hardware strategically located in a vehicle), analyzing the data, and appropriately activating hardware to take actions protecting vehicle occupants. Typical controllers are vehicle control modules, smart phones, black boxes, PCs, lap tops, smart pads, integrated circuits, removable control cards, and/or the like.

The controllers can have subsystems adapted to receive signals from sensors. Sensor input receiving subsystems can include adaptors that convert analog signals to digital signals (A to D conversion) or the sensors themselves may provide a digital output to the controller. The controllers can have one or more inputs to receive signals from, e.g., light intensity sensors, relative humidity detectors, temperature sensors, video cameras, light frequency sensors, pressure sensors, mechanical position sensors, infrared intensity and/or imaging sensors, micro switches, data entry devices, remote control devices, global positioning devices, and/or the like.

The controllers can have subsystems adapted to send signals, e.g., to activate or control accessories. For example, the logic circuits of the controller can send signals through an interface to control mechanical hardware or to initiate communications with other digital systems, occupants, or external parties. The controller output can control actuators, motors, heaters, stepper motors, linear motors, vehicle environment control systems, fans, baffles, valves, solenoids, and or the like, e.g., to adjust the temperature of the vehicle interior or allow egress of occupants from the vehicle. The controller output can include communications to digital devices or persons. For example, the controller can initiate an audio file (language or siren) informing occupants of danger though a speaker or public address system. Outputs can actuate visual signals, e.g., including warning lights, graphic indicia, or video display. The outputs can broadcast the hazard warning to external parties, such as vehicle owners or first responders, e.g., through radio or cell phone messages.

II. Methods.

Figure 2:
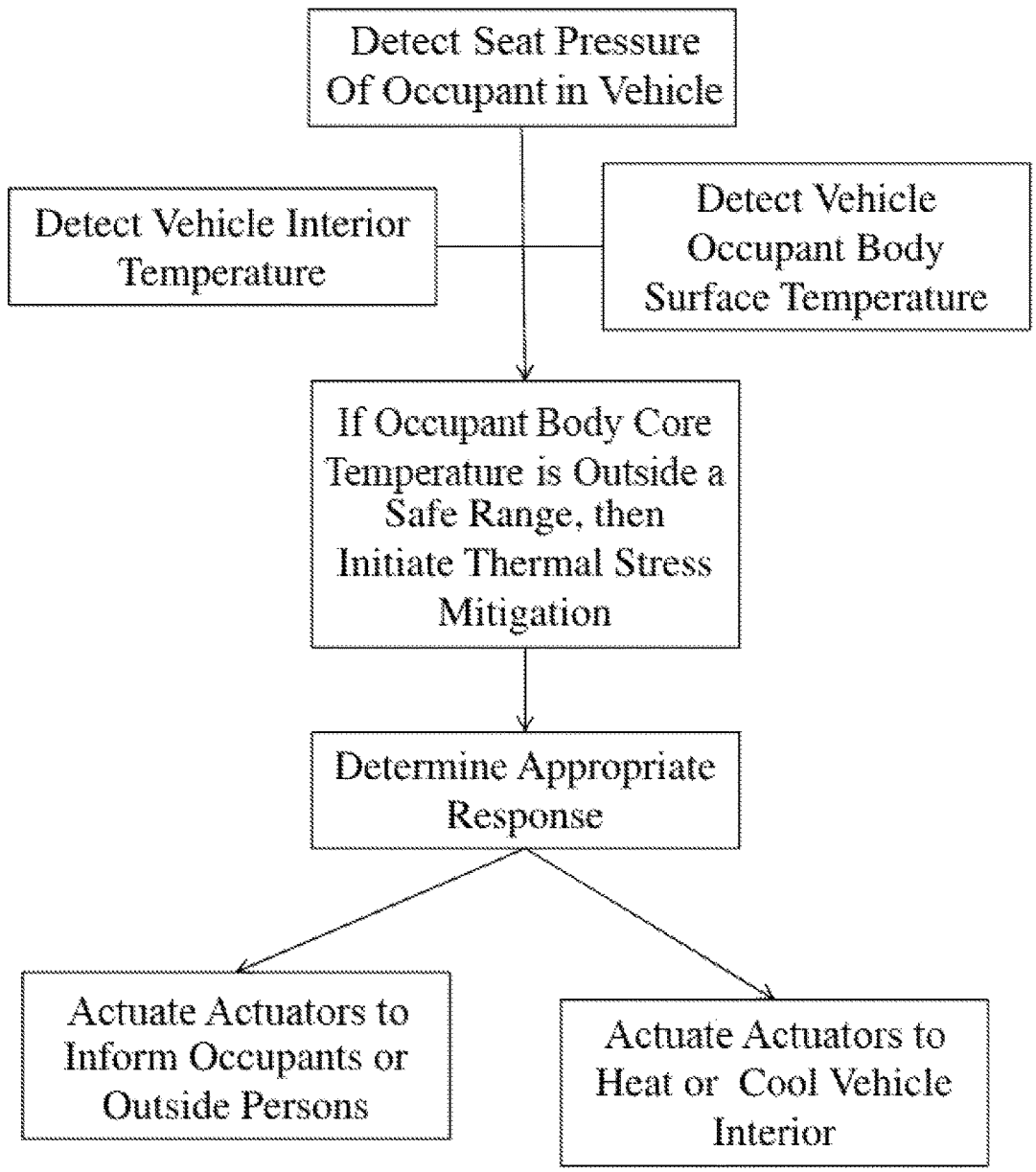
FIG. 2 is a block flow diagram of methods for determining a heat stress condition and determination of appropriate steps to take.

The present inventions include methods of detecting and mitigating dangers of heat stress to occupants of a vehicle. A typical method, as shown in FIG. 2, includes detecting the presence of an occupant in a vehicle, detecting the temperature of the internal compartment of the vehicle, detecting the body surface temperature of the occupant, analyzing the detected conditions to determine if a thermal stress threat is present for the occupant, determining an appropriate level of response to mitigate the thermal stress threat, and instructing appropriate actuators to reduce the temperature in the vehicle compartment.

Detecting the presence of an occupant in a vehicle can include interpretation of sensor input by the controller. Determination of vehicle occupancy can be by detection of one signal, or two or more. For example, occupancy can be detected by a simple pressure detector in a passenger seat, a motion detector, an IR light detector, RFID or Bluetooth signal detection, or a sound detector. However, these simple methods of occupant detection can be subject to substantial false positive results. More reliable results can be provided with combinations of detected signals. For example, occupant detection can be by a combination of seat pressure detection and an IR presence at that seat location, IR detection and motion detection (e.g., characteristic active or passive ultrasonic detection), face or body silhouette detection and seat pressure detection, voice recognition and seat pressure detection, and/or other combinations of the above. In many cases, detecting the occupant also detects the location of one or more occupants within the vehicle, and/or the type of occupant (size, age, etc.).

Detecting vehicle interior temperature can be by use of the sensors discussed above with regard to the inventive systems. Typically a thermometer (IR sensor, bimetalic strip, thermistor, etc.) is wired to the sensor input of the controller. One or more of the thermometers can be located to take the temperature of the ambient interior air, air coursing through the AC or venting systems, or interior vehicle surfaces. Signals from the thermometers can be transmitted to the controller for consideration in determining the level of thermal stress threat. In some embodiments, interior temperatures are not used, or have substantially less weight in determining thermal stress threat than the direct evaluation of an occupant body surface temperature.

Detecting the temperature of a vehicle occupant is the most direct and accurate way to evaluate the thermal stress condition of the occupant. Ultimately, the present systems are intended to avoid or remove dangerous thermal stress from an occupant. In one aspect of the invention, an occupant can self-report a thermal stress condition to the controller, e.g., through a user interface. For example, a heat emergency button can be provided to occupants. More typically the present methods gather sensor signals to make a considered determination of thermal stress, e.g., for occupants incapable of self-reporting (such as, elderly, disabled, infants, pets, etc.). The body temperature of an occupant is typically detected by a determination of a skin surface temperature of the occupant. Such a determination can be by thermometer contact with the skin or by IR detection.

In preferred embodiments, an infrared signal from the occupant's body can be used to determine a surface temperature, and infer a body temperature. The IR sensor can have a narrow field of view, e.g., directed to a position at a seat where an occupant's skin (e.g., face) would be expected. Alternately, the IR sensor can collect an array of readings (e.g., using an IR imaging device). IR array pattern can be reviewed to detect the location of one or more occupants. Occupant temperatures can be evaluated with regard to a peak temperature or average temperature of the occupant. The IR array output can be reviewed to identify a body or facial pattern, then the indicated temperature for a select body surface (e.g., forehead, hand, cheek) can be noted.

If an occupant is in the vehicle, and if a temperature (ambient or body) suggests there may be a danger of thermal stress to the occupant, the controller can direct one or more actuators to reverse, stop or prevent an thermal stress condition in the vehicle or occupant. Instructions to actuators may be initiated solely on the detection of a certain vehicle temperature threshold and/or occupant temperature threshold. For example, interior temperature reduction activities can be initiated if the detected occupant body temperature suggests essentially febrile conditions (e.g., an internal body temperature of 99° F. or more). Temperature reduction activities can directed if the detected body surface temperature is 90° F., 95° F., 98° F., 99° F., 100° F., 103° F., or more. Temperature reduction activities can directed if the detected body surface temperature is 95° F., 98° F., 99° F., 100° F., 103° F., or more, and the interior temperature or body surface temperature has a rising trend, e.g., increasing by 1° F. per 5 minutes, 3 minutes, 1 minute, or 0.5 minutes. With regard to clod conditions, interior heating activities can be initiated if the detected occupant body temperature suggests essentially hypothermic conditions (e.g., an internal body temperature of 96° F. or less). Interior warming activities can directed if the detected body surface temperature is 97° F., 96° F., 94° F., 92° F., 90° F., 88° F., or less. Heating activities can directed if the detected body surface temperature is less than 98° F., 97° F., 95° F., 93° F., 90° F., 88° F., or less, and the interior temperature or body surface temperature has a cooling trend, e.g., decreasing by 1° F. per 5 minutes, 3 minutes, 1 minute, or 0.5 minutes Once it is determined that thermal stress conditions exist in the vehicle (e.g., occupancy, interior temperature, and occupant temperature), a temperature adjustment activity can be directed by the controller to one or more appropriate actuators. For example, in a stationary car (detected by, e.g., speedometer or GPS signal) with a rising internal temperature of more than 90° F. and occupant body surface temperature of 90° F. or more, the controller can instruct outside air fans to exchange internal for external air. If a high external air temperature is detected (e.g., not at least 5° F. less than the interior temperature), then the controller could also include a warning (cell phone, audio signal, flashing light) to suggest the occupant leave the car or turn on an air conditioning system. In a moving car with a rising internal temperature of more than 90° F. and occupant body surface temperature of 90° F. or more, the controller can instruct the vent damper motors to open vents, outside air fans to exchange internal for external air, and/or turning on or up the AC system. Should the surface body temperature of an occupant reach a critical threshold (e.g., 98° F., 100° F., 103° F., 105° F., or more) the controller can send any combination of instructions depending on the vehicle condition (e.g., running or moving), including, e.g., opening windows, running AC, opening vents, running fans. In a cooling environment situation, e.g., with a decreasing interior temperature of less than 60° F. and occupant body surface temperature of 70° F. or less, the controller can instruct activation of vehicle heating systems. Should the surface body temperature of an occupant go below a critical threshold (e.g., 65° F., 55° F., 45° F., 35° F., or less) the controller can send any combination of instructions depending on the vehicle condition (e.g., running or moving), including, e.g., closing windows, running the motor and/or heater, energizing seat heaters, and/or the like.

Under any of the heat stress conditions described above, the controller can be configured to communicate with occupants of external parties. The communications can be proportionate and/or sequential depending on the conditions. For example, initial indications of early thermal stress conditions may be signaled with a flashing light or audio warning beep. More severe conditions can elicit a louder audio signal and direct actions to mitigate a changing temperature. More severe conditions, such as a stationary vehicle, rising interior temperatures above 95° F., and/or a body surface temperature above 98° F., can prompt a more urgent response, such as discharging a siren, a public address broadcast, and/or initiating a cellular phone call to a pre-designated phone number or emergency service.

EXAMPLES

The following examples are offered to illustrate, but not to limit the claimed invention.

Example-1 Vehicle Heat Stress Avoidance System

An automobile is outfitted with an internal temperature sensor, seat cushion pressure sensors, and an infrared video camera to detect the presence of vehicle occupants and environmental conditions.

The automobile has an air conditioning system, auto start, motorized windows, visual and audio signals, and a cellular phone.

The above sensor and actuator devices are connected to the input and output interfaces, respectively, of a controller. The controller is configured to detect the presence of any vehicle occupant and the surface body temperature of the occupant.

When the interior cabin temperature of the automobile is above 85° F., the controller energizes from a power saving sleep mode, and instructs activation of the IR sensor camera. The resultant array of video images show an outline of an infrared pattern indicative of a human occupant in a rear seat, which has a positive seat pressure signal corroborating the presence of an occupant. The video image is evaluated within the field of the human pattern for a peak temperature and for the average temperature on the face area of the human. The controller receives GPS data suggesting the automobile is not in motion.

As the interior temperature surpasses 90° F. in 10 minutes, the controller evaluates the IR array data to find the occupant average face surface temperature is above 95° F. The controller energizes a flashing warning light and associated beep. As the interior temperature surpasses 100° F., the controller evaluates the IR array data to find the occupant average face surface temperature is above 98° F. The controller opens windows and turns on vent fans.

If the conditions of heat stress continue to increase (or the windows fail to open), the controller could sequentially initiate an internal alarm commanding exit from the automobile, a public address alarm, and a phone call to the automobile owner and/or emergency service.

Example-2 Vehicle Cold Stress Avoidance System

An automobile is outfitted with an internal temperature sensor, seat cushion pressure sensors, and an infrared video camera to detect the presence of vehicle occupants and environmental conditions.

The automobile has an heating system, auto start, motorized windows, visual and audio signals, and a cellular phone.

The above sensor and actuator devices are connected to the input and output interfaces, respectively, of a controller. The controller is configured to detect the presence of any vehicle occupant and the surface body temperature of the occupant.

When the interior cabin temperature of the automobile is below 55° F., the controller energizes from a power saving sleep mode, and instructs activation of the IR sensor camera. The resultant array of video images show an outline of an infrared pattern indicative of a human occupant in a passenger seat, which has a positive seat pressure signal corroborating the presence of an occupant. The video image is evaluated within the field of the human pattern for a peak temperature and for the average temperature on the face area of the human. The controller receives vehicle CPU data suggesting the automobile motor is not running.

As the interior temperature falls below 50° F. in 10 minutes, the controller evaluates the IR array data to find the occupant average face surface temperature is below 65° F. The controller energizes a flashing warning light and associated beep. As the interior temperature falls below 45° F., the controller evaluates the IR array data to find the occupant average face surface temperature is below 55° F. The controller assures windows are closed, starts the car and turns on the heating system.

If the conditions of cold stress continue to get worse, or the surface temperature of the occupant does not improve, the controller could sequentially initiate an internal alarm commanding exit from the automobile, a public address alarm, and a phone call to the automobile owner and/or emergency service.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A system for preventing excessive thermal stress exposure to any occupants of a vehicle, the system comprising:
   an occupancy sensor;
   an occupant body surface temperature sensor configured to detect a body surface temperature of an occupant in the vehicle;
   an actuator; and,
   a controller configured to receive signals from the occupancy sensor and from the occupant body surface temperature sensor,
   wherein the controller is configured to determine an occupant body core temperature based on the signals from the occupant body surface temperature sensor when the controller receives an occupant present signal from the occupancy sensor; and,
   wherein the controller is configured to activate the actuator when the determined occupant body temperature falls outside a preset temperature range.

2. The system of claim 1, further comprising a vehicle interior temperature sensor, and wherein the actuator is not activated unless an interior temperature detected by the interior temperature sensor falls outside a preset range.

3. The system of claim 1, wherein the occupancy sensor comprises a microphone or a seat pressure sensor.

4. The system of claim 1, wherein the occupant body temperature sensor comprises an infrared light sensor configured to measure a temperature of an occupant body surface.

5. The system of claim 4, wherein the controller is configured to receive the occupant body surface temperature signal and determine a body surface temperature ranging from 25° C. to 45° C.

6. The system of claim 5, wherein the controller activates the actuator when the determined occupant body core temperature exceeds 39° C. or falls below 35° C.

7. The system of claim 1, wherein the actuator is selected from the group consisting of: a cell phone, a motorized window, a heater, a vent fan, and a siren.

8. The system of claim 1, wherein the occupant body temperature sensor comprises an infrared sensor directed to a position on the occupant's skin, or the occupant body temperature sensor comprises an IR sensor configured to detect an array of IR data and to select a body surface of the occupant and detect a temperature of the selected body surface.

9. The system of claim 1, wherein the system includes both a vehicle interior temperature sensor and an occupant body temperature sensor.

10. The system of claim 1, wherein the actuator is activated only when an interior temperature of the vehicle exceeds a preset temperature.

11. The system of claim 1, wherein the system further comprises a vehicle interior temperature sensor communicating with the controller, and the occupant body core temperature is inferred from the vehicle interior temperature and the occupant body surface temperature.

12. A method of preventing excessive thermal stress exposure to an occupant of a vehicle, the method comprising:
    providing a system comprising:
    an occupancy sensor;
    an occupant body temperature sensor configured to detect a body surface temperature of the occupant;
    an actuator; and,
    a controller configured to receive signals from the occupancy sensor and from the occupant body surface temperature sensor;
    receiving an occupant present signal from the occupancy sensor;
    determining an occupant body core temperature based on a signal from the occupant body surface temperature sensor; and
    activating the actuator when the determined occupant body core temperature falls outside a preset temperature range.

13. The method of claim 12, wherein said receiving an occupant present signal comprises the controller receiving a signal from an element selected from the group consisting of: an infrared light sensor, a pressure sensor, and ultrasonic microphone, and an audio microphone.

14. The method of claim 12, wherein said determining the occupant body surface temperature comprises determining an infrared light spectrum emitted from a surface of the occupant.

15. The method of claim 12, wherein said activating the actuator is selected from the group consisting of: energizing an electric window motor, energizing a heater, energizing a fan motor, dialing a phone number, and energizing an audio speaker.

16. The method of claim 12, wherein the occupant body temperature sensor comprises an infrared sensor directed to a position on the occupants skin, or the occupant body temperature sensor comprises an IR array sensor configured to detect an array of IR data, to select a body surface of the occupant and detect a temperature of the selected body surface.

17. The method of claim 12, wherein the system includes both a vehicle interior temperature sensor and an occupant body temperature sensor.

* * * * *